US00PP18813P3

(12) United States Plant Patent
Conibear

(10) Patent No.: US PP18,813 P3
(45) Date of Patent: May 13, 2008

(54) ***LUPINUS* PLANT NAMED 'BLOSSOM'**

(50) Latin Name: *Lupinus hybridus*
Varietal Denomination: Blossom

(76) Inventor: Sarah Frances Conibear, West Country Nurseries Donkey Meadow, Woolsery, Bideford, Devon EX39 5QH (GB)

( * ) Notice: Subject to any disclaimer, the term of this patent is extended or adjusted under 35 U.S.C. 154(b) by 0 days.

(21) Appl. No.: 11/474,073

(22) Filed: Jun. 23, 2006

(65) Prior Publication Data

US 2007/0300342 P1 Dec. 27, 2007

(51) Int. Cl.
*A01H 5/00* (2006.01)

(52) U.S. Cl. ..... Plt./263.1

(58) Field of Classification Search ..... Plt./263, Plt./263.1
See application file for complete search history.

(56) References Cited

PUBLICATIONS

USDA Plants Database for *Lupinus hybridus* Lem. [online], [retrieved on Jul. 18, 2007]. Retrieved from the Internet <http://plants.usda.gov/java/jsp/classification/classification_print_friendly.jsp?fileNamePF=cl...> one page.*

* cited by examiner

*Primary Examiner*—Kent Bell
*Assistant Examiner*—June Hwu
(74) *Attorney, Agent, or Firm*—The Webb Law Firm

(57) ABSTRACT

'Blossom' is a new variety of *Lupinus hybridus* that exhibits numerous and large-shaped pinkish-colored flowers.

2 Drawing Sheets

Botanical classification: *Lupinus hybridus*.
Varietal denomination: 'Blossom'.

BACKGROUND OF THE INVENTION

The present invention comprises a new and distinct cultivar of *Lupinus hybridus* known by the varietal name 'Blossom'. The new variety was developed in Great Britain. The new variety is a result of cross breeding a Russell Hybrid *Lupinus* Seedling #WCL 045/96 (female parent) (unpatented) and an unknown *Lupinus* male parent (unpatented). The purpose of the breeding program was to develop a cultivar that exhibited improved color, habit, and bloom form from other *Lupinus* varieties known to the breeder. The new variety exhibits better color, more flowers, and has flowers more closely packed on the spike than *Lupinus* variety. 'The Chatelaine' (unpatented). The new variety is similar in growth habit to its female parent, but differs in flower color. The new variety was first asexually reproduced by basal cuttings/tissue culture in Great Britain. The new variety has been trail and field tested and has been found to retain its distinctive characteristics and remain true to type through successive asexual propagations. Characteristics that distinguish the new variety from other known to the breeder include:

- Clear and intense flower color;
- Flower form — papilionaceous, with closely packed and large flowers; and
- Vigorous growth habit.

The new variety was grown in open soil with additional organic fertilizer applied. The new variety initiates and develops roots in 21 days at 15° C. A finished and flowering plant is produced in 36 weeks in a 21 cm container. The new variety exhibits sparse, but thick roots, that exhibit some branching.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
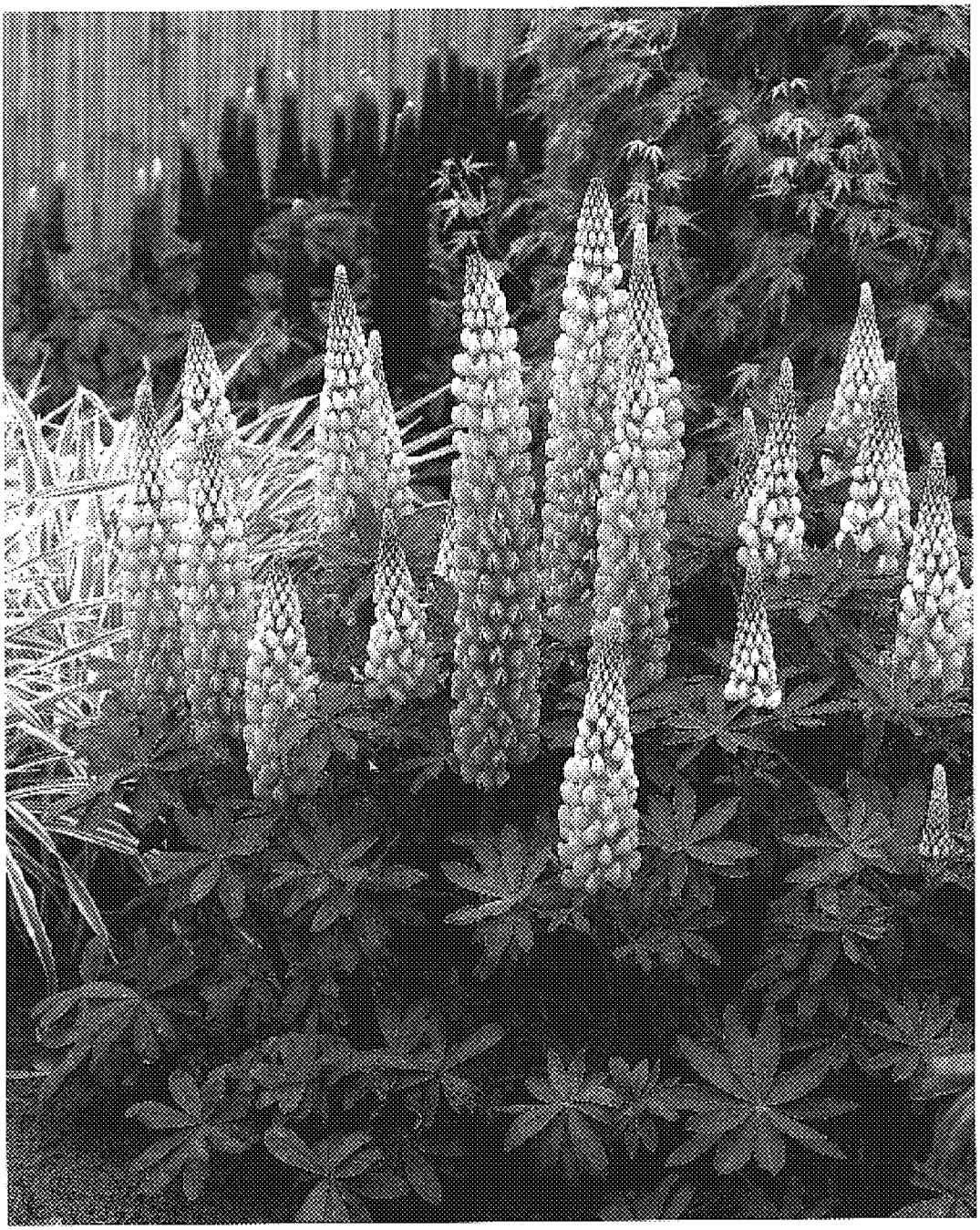
FIG. 1 is a photographic image of multiple plants of the new variety.
Figure 2:
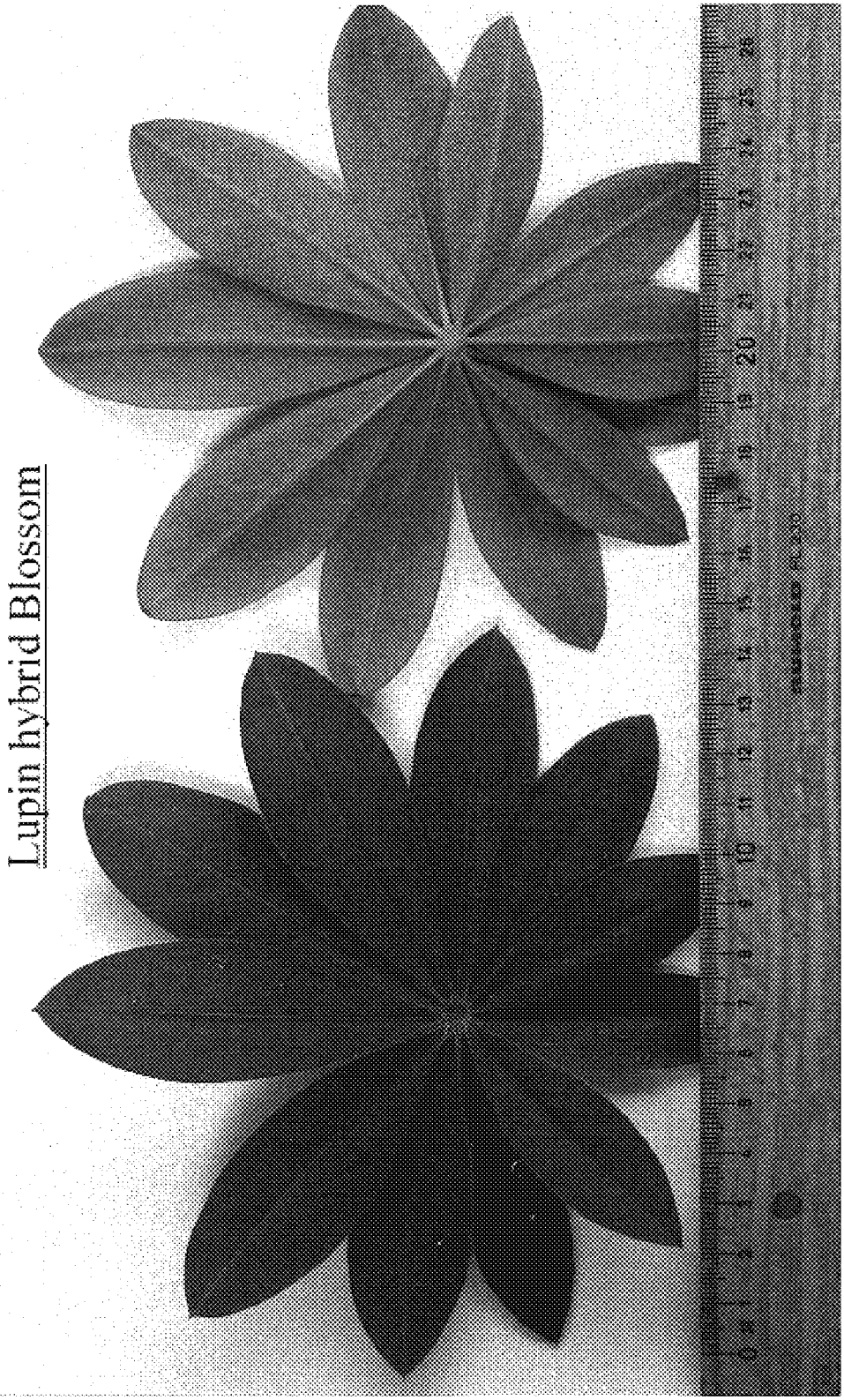
FIG. 2 is a close-up photograph of both surfaces of the leaves of the new variety.

The following detailed description sets forth the characteristics of the new cultivar. The data which defines these characteristics were collected by asexual reproductions carried out in Great Britain. The color readings were taken outside under natural daylight. Color references are primarily to the R.H.S. Colour Chart of The Royal Horticultural Society of London.

PLANT

Form: Mounded and symmetrical.
Stem:
  *Diameter.*—15 mm.
  *Color.*—Between 144B and 144C.
  *Texture.*—Slightly hirsute, smooth with longitudinal ridges.
  *Pubescence.*—Slightly to medium.
Height: 80 cm.
Plant diameter: 55 cm.
Vigor: Good.
Branching habit: Free.
Lateral branches:
  *Diameter.*—9 mm.
  *Internode length.*—6.8 cm.

*Texture.*—Lightly hirsute, smooth with longitudinal ridges.
*Pubescence.*—Present.
*Color.*—144B.

Foliage:
*Arrangement.*—Ascending spiral.
*Length of leaf stalk.*—Basal foliage: 26 cm. Stem foliage: 16 cm.
*Size of leaf* (*overall*).—Length: 16 cm. Width: 15 cm.

Leaflets:
*Shape of leaflet.*—Oblanceolate.
*Number.*—12.
*Width.*—2.5 cm.
*Length.*—7.3 cm.
*Shape of apex.*—Acute.
*Shape of base.*—Cuneate.
*Aspect.*—Horizontal presentation.
*Margin type.*—Smooth; entire.
*Pubescence.*—Upper surface: None present. Lower surface: Slight.
*Color.*—Young leaflet: Upper surface: Varies between 137B and 137C. Lower surface: 137C and 138B. Mature leaflet: Upper surface: Varies between 137A and 137B. Lower surface: Varies between 137C and 137D.
*Petiole.*—Shape: Flattened and round. Length: Basel leaf: 26 cm. Stem leaf: 16 cm. Diameter: 5 mm. Color: 144B.
*Venation.*—Central; mid-rib; colored the same as the leaflets.

FLOWER

Bud (described when buds were just beginning to open):
*Shape.*—Napiform.
*Diameter.*—9 mm.
*Length.*—18 mm.
*Color.*—36A.

Natural flowering season: May through July in The Netherlands.

Flower type and habit: Spike.
*Number of flowers per spike.*—187.
*Length of spike.*—45 cm.
*Diameter of spike.*—11.9 cm.

Corolla:
*Form.*—Zygomorphic
*Petals.*—Standard Petals: Number: 2-fused. Length: 20 mm. Width: 12 mm. Shape: Ovate. Aspect: Parallel to spike. Margin: Smooth and entire. Wing Petals: Number: 2. Length: 20 mm. Width: 14 mm. Shape: Ovoid to kidney-shaped. Aspect: Slightly tilted upward. Margin: Smooth and entire. Keel Petals: Number: 2-fused. Length: 18 mm. Width: 9 mm. Shape: Lingulate. Aspect: Located within wing petals and pointing upwards. Margin: Smooth and entire. Texture and appearance: Smooth and satin-like. Standard Petal color: When opening: Upper surface: Between 55C and 55D. Lower surface: 55D. Fully opened: Upper surface: Between 55B and 55C. Lower surface: Between 55C and 55D. Wing Petal color: When opening: Upper surface: Between 55C and 55D. Lower surface 55D. Fully opened: Upper surface: Between 55B and 55C. Lower surface: Between 55C and 55D. Keel Petal color: When opening: Both surfaces: 56C. Fully opened: Both surfaces: 56C.
*Throat* (*revealed when parting the standard petal from the keep petal*).—Color: 4D. Texture: Smooth and satin-like.

Calyx:
*Form.*—Two unequal halves.
*Length.*—8 mm.
*Diameter.*—15 mm.
*Sepal shape.*—Elliptic.
*Sepal margin.*—Smooth and entire.
*Sepal texture.*—Smooth with slight pubescence.
*Sepal size.*—Length: 8 mm. Width: 5 mm.
*Sepal color: Upper surface: Varies between* 149C and 149D. Lower surface: 149D.

Fragrance: Slight.

Disease resistance/susceptibility: Susceptible to powdery mildew.

Temperature tolerance: Medium to good.

Lasting quality: Medium to good.

REPRODUCTIVE ORGANS

Stamens:
*Number* (*per flower*).—There are two groups. A first group with 6 stamens and a second group with 4 stamens.
*Filaments.*—Length: First group: 4 mm. Second group: 8 mm. Fused: Yes.
*Anthers.*—Shape: First group: Pencil-like. Second group: Arrow-like. Length: First group: 2 mm. Second group: 0.8 mm. Color: First group: 169B. Second group: Varies between 23A and 23B.
*Pollen.*—Color: 23A. Amount: Plentiful.
*Pistils.*—Length: 11 mm. Style: Length: 11 mm. Color: 150C. Stigma: Shape: Spherical. Color: 150C.
*Seed/Fruit production.*—Description of conditions when produced: Produced freely. Color: Varies between 165A and 165B. Size: 1.0 mm. Number: Approximately 2000 per plant.

I claim:

1. A new and distinct variety of *Lupinus hybridus* plant named 'Blossom' as is herein described and illustrated.

* * * * *